_United States Patent_ [19]

Franz

[11] 4,084,953

[45] Apr. 18, 1978

[54] N-HYDROXY-N-PHOSPHONOMETHYLG-LYCINES AND THE HERBICIDAL USE THEREOF

[75] Inventor: John E. Franz, Crestwood, Mo.

[73] Assignee: Monsanto Company, St. Louis, Mo.

[21] Appl. No.: 776,061

[22] Filed: Mar. 9, 1977

[51] Int. Cl.$^2$ ............................ A01N 9/36; C07F 9/38
[52] U.S. Cl. ............................ 71/86; 260/501.12; 260/502.5
[58] Field of Search .......................... 260/502.5; 71/86

[56] References Cited

U.S. PATENT DOCUMENTS

| | | | |
|---|---|---|---|
| 3,288,846 | 11/1966 | Irani et al. | 260/502.5 |
| 3,853,530 | 12/1974 | Franz | 260/502.5 |
| 3,888,915 | 6/1975 | Alt | 260/502.5 |
| 3,933,946 | 1/1976 | Gaertner | 71/86 |

*Primary Examiner*—Joseph E. Evans
*Attorney, Agent, or Firm*—Donald W. Peterson; William T. Black

[57] ABSTRACT

This disclosure relates to N-hydroxy-N-phosphonomethylglycine and the herbicidally acceptable salts thereof which are useful as herbicides to control undesired plants.

6 Claims, No Drawings

N-HYDROXY-N-PHOSPHONOMETHYLGLYCINES AND THE HERBICIDAL USE THEREOF

This invention relates to new organic chemical compounds. More particularly, this invention is concerned with N-hydroxy-N-phosphonomethylglycine and the herbicidally acceptable salts thereof. These compounds have been found to display useful herbicidal activity when applied to certain varieties of weeds or undesired plants.

U.S. Pat. No. 3,933,946 discloses trimethyl-N-hydroxy-N-phosphonomethylglycinate and methyl-N-hydroxy-N-(diallyloxyphosphinylmethyl)glycinate and the herbicidal activity thereof. These compounds, however, have only weak herbicidal activity. For example, the former at 4.48 kg/ha gave only 26–49% kill on morning glory and barnyard grass but was not effective against any of the remaining species in the test. The latter compound when applied at 4.48 kg/ha after 4 weeks showed 50–74% kill on morning glory, 75–99% kill on barnyard grass and 26–49% kill on the remaining species in the test. It has been discovered unexpectedly that N-hydroxy-N-phosphonomethylglycine and its herbicidally acceptable salts have substantially greater activity against these weed species than the triester derivatives.

The compounds of the instant invention are N-hydroxy-N-phosphonomethylglycine and its herbicidally acceptable salts. The parent acid compound is represented by the structural formula

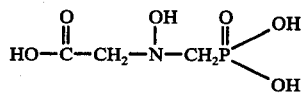

This novel acid is prepared by the reaction of N-hydroxyglycine with phosphorous acid and formaldehyde employing a strong acid such as hydrochloric acid as the catalyst.

The N-hydroxy-N-phosphonomethylglycine is usually employed in the acid form in herbicidal compositions and in herbicidal uses. The acid can also be converted into its herbicidally acceptable salts and employed in such form inasmuch as such salts are usually more soluble and the formations are easier to prepare and to employ. Such herbicidally acceptable salts can be, for example, the alkali metal salts, the alkaline earth metal salt and the ammonium and lower aliphatic ammonium salts of the free acid. Lower aliphatic as employed herein include mono, di and tertiary ammonium wherein each group contains 1 to 8 carbon atoms and includes alkyl, alkenyl and alkynyl groups.

The following examples further illustrate the invention, all parts being parts by weight unless otherwise expressly set forth.

EXAMPLE 1

Paraformaldehyde (2.05 g., .025 mol), water (5 ml), concentrated hydrochloric acid (7.5 ml), N-hydroxyglycine (2.3 g, 0.025 mol) and phosphorous acid (2.05 g, 0.025 mol) were charged into a glass reactor and stirred at room temperature (25° C.) for approximately 16 hours. The mixture was heated to 68°–70° C. with stirring for 7 ½ hours. The reaction mixture was then concentrated at reduced pressure, 5 ml of water added to the residue and the solution again concentrated under reduced pressure to yield a viscous residue. Ethanol (30 ml) and then propylene oxide (1.6 g, .034 mol) were added to the viscous liquid. The mixture was allowed to stand at ambient temperature for a few minutes and the supernatant liquid was decanted from a tacky precipitate. Fresh ethanol was added and the mixture allowed to stand overnight at room temperature. The precipitate was ground under several portions of fresh ethanol until a granular powder was obtained. The powder was washed with ether and then dried under vacuum (0.5 mm Hg, yield 2.4 g). Nuclear magnetic resonance spectral analysis indicated that the material was essentially N-hydroxy-N-phosphonomethylglycine contaminated with aminomethylphosphonic acid and some ethanol or ether. The main portion of the 2.4 g of the above solid (about 2.2 g) was washed three times with small portions of water to remove a yellow impurity and most of the aminomethylphosphonic acid. The resultant white residue was dried at ambient temperature and at reduced pressure (10–20 mm Hg). The yield of recovered N-hydroxy-N-phosphonomethylglycine which contained a small amount of aminomethylphosphonic acid (less than 3%) was 1.3 g, M.P. 133°–5° C. with decomposition. This material was tested as a herbicide in Example 2.

A small portion of the above material was recrystallized from a small quantity of water and dried at 0.5 mm Hg (M.P. 43°–4° C. with decomposition). The recrystallized material was pure N-hydroxy-N-phosphonomethylglycine and gave the following analysis.

Calc'd. for $C_3H_8NO_6P$: C, 19.47; H, 4.36; N, 7.57; P, 16.73 Found: C, 19.21; H, 4.50; N, 7.50; P, 16.90.

EXAMPLE 2

The post-emergent or contact herbicidal activity of the compounds of this invention is demonstrated by means of greenhouse testing. A good grade of top soil is placed in aluminum pans and compacted to a depth of ⅜ to ½ inch (0.95 to 1.27 cm.) from the top of the pan. A predetermined number of seeds of each of several broadleaf and grassy plant species are placed on top of the soil in the pans. The seeds are covered with soil and the pans leveled. The pans are then placed on a sand bench in the greenhouse and watered from below as needed. After the plants are the desired age, each pan of plants is sprayed with a given volume of solution containing the candidate chemical in the amount equivalent to the application rates cited below. This solution is prepared from an aliquot of a 1% solution of the candidate compound in acetone or other suitable solvent, a known amount of cyclohexanone-emulsifying agent mix, and sufficient water to make up to volume. The emulsifying agent is a mixture comprising 35 weight percent butylamine dodecylbenzene sulfonate and 65 weight percent of a tall oil-ethylene oxide condensate having about 6 moles of ethylene oxide per mole of tall oil. The injuries to the plants are then observed approximately 28 days later and the results are recorded. WAT in Table 1 means weeks after treatment.

The post-emergence herbicidal index used in the table is as follows:

| Plant Response | Index |
| --- | --- |
| 0 – 24% Control | 0 |
| 25 – 49% Control | 1 |
| 50 – 74% Control | 2 |
| 75 – 99% Control | 3 |

| Plant Response | Index |
|---|---|
| 100% Kill | 4 |

TABLE 1

| Cpd. | kg WAT h | Plant Species | | | | | | | | | | |
|---|---|---|---|---|---|---|---|---|---|---|---|---|
| | | A | B | C | D | E | F | G | H | I | J | K |
| 1 | 4  5.6 | 3 | 2 | 1 | 3 | 4 | 2 | 2 | 3 | 3 | 2 | 3 |

The plant species utilized in the test are identified by letter in accordance with the following legend:
A - Canada Thistle
B - Cocklebur
C - Velvet Leaf
D - Morning Glory
E - Lambsquarters
F - Smartweed
G - Nutsedge
H - Quackgrass
I - Johnson Grass
J - Downy Brome
K - Barnyard Grass In a separate test it was found that aminomethylphosphonic acid at 4.48 kg/ha was active against only species B, C, D and F having a 1 rating.

For the sake of brevity and simplicity, the term "active ingredient" is employed hereinafter in this specification to describe the N-hydroxy-N-phosphonomethylglycine and the herbicidally acceptable salts thereof as hereinbefore described.

In herbicidal compositions, the active ingredient can be admixed with one or more adjuvants which can be solid or liquid extenders, carriers, diluents, conditioning agents and the like. The herbicidal formulations comprise wettable powders, aqueous suspensions or solutions, dust formulations, emulsifiable oils and solutions in solvents. In general, these formulations can all contain one or more surface-active agents.

Surface-active agents which can be used in herbicidal formulations are well known to those skilled in the art and have been well documented in U.S. Patents, bulletins and textbooks.

The preparation, formulations and particle size of the wettable powders, aqueous suspensions or solutions, dusts, emulsifiable oils and solutions in solvents are also well known to those skilled in the art and well documented.

The active ingredient is usually present in the herbicidal compositions in a range of about 0.5 to 95 parts by weight per 100 parts by weight of wettable powder and dust formulations; 5 to 95 parts by weight per 100 parts by weight water in water suspensions or solutions. Formulations containing other than the above quantities of active ingredient can easily be prepared by those skilled in the art.

Application of the herbicidal compositions of this invention to the plant is well-known to those skilled in the art. The application of liquid and particulate solid herbicidal formulations to the above-ground portions of plants can be carried out by conventional methods, e.g., power dusters, boom and hand sprayers and spray dusters.

The active ingredient can be admixed with one or more adjuvants which can be solid or liquid extenders, carriers, diluents, conditioning agents and the like to form herbicidal compositions. Herbicidal formulations contain the active ingredients of this invention with wettable powders, aqueous suspensions or solutions, dust formulations, emulsifiable oils and solutions in solvents. In general, these formulations can all contain one or more surface-active agents. Herbicidal mixtures are applied at a rate of 1 to 50 kilograms per hectare of active ingredient for general herbicidal effect.

While the illustrative embodiments of the invention have been described hereinbefore with particularity, it will be understood that various other modifications will be apparent to and can readily be made by those skilled in the art without departing from the scope and spirit of the invention. Accordingly, it is not intended that the scope of the claims appended hereto be limited to the examples and descriptions set forth herein but rather the claims be construed as encompassing all the features of patentable novelty which reside in the present invention including all features which would be treated as equivalents thereof by those skilled in the art to which the invention pertains.

What is claimed is:

1. N-hydroxy-N-phosphonomethylglycine and the herbicidally acceptable salts thereof.

2. A compound of claim 1 which is N-hydroxy-N-phosphonomethylglycine.

3. A herbicidal composition comprising a herbicidally inert adjuvant and a herbicidally effective amount of a compound of claim 1.

4. A herbicidal composition comprising a herbicidally inert adjuvant and a herbicidally effective amount of the compound of claim 2.

5. A herbicidal method which comprises applying to plants a herbicidally effective amount of a compound of claim 1.

6. A herbicidal method which comprises applying to plants a herbicidally effective amount of the compound of claim 2.

* * * * *